United States Patent [19]

Pomplun et al.

[11] Patent Number: 4,816,094
[45] Date of Patent: Mar. 28, 1989

[54] METHOD OF PRODUCING A HEAT SHRINKABLE ELASTOMER AND ARTICLES UTILIZING THE ELASTOMER

[75] Inventors: William S. Pomplun; Rodney C. Christianson, both of Neenah; Mark C. Jacobs, Appleton, all of Wis.; Attila Matray, Roswell, Ga.

[73] Assignee: Kimberly-Clark Corporation, Neenah, Wis.

[21] Appl. No.: 129,913

[22] Filed: Dec. 4, 1987

Related U.S. Application Data

[63] Continuation of Ser. No. 849,916, Apr. 8, 1986, abandoned, which is a continuation-in-part of Ser. No. 606,082, May 1, 1984, abandoned.

[51] Int. Cl.$^4$ .................. B29C 55/04; B32B 31/04
[52] U.S. Cl. ...................... 156/85; 156/160; 156/229; 156/244.24; 156/299; 264/164; 264/229; 264/230; 264/288.4; 264/291; 264/342 RE
[58] Field of Search ............... 264/288.4, 290.2, 290.5, 264/291, 230, 288.8, 164, 229, 342 RE, 284.6; 156/84–86, 160, 229, 244.11, 250, 244.17, 244.18, 244.24, 259, 264, 265, 272.2, 275.7, 297, 299, 301, 163, 164; 604/385

[56] References Cited

U.S. PATENT DOCUMENTS

| | | | |
|---|---|---|---|
| 3,479,425 | 11/1969 | Lefevre et al. | 264/171 |
| 3,536,803 | 10/1970 | Epstein | 264/210 |
| 3,557,265 | 1/1971 | Chisholm et al. | 264/47 |
| 3,639,917 | 2/1972 | Althouse | 2/270 |
| 3,819,401 | 6/1974 | Massengale et al. | 156/85 |
| 3,912,565 | 10/1975 | Koch et al. | 156/85 |
| 4,152,387 | 5/1979 | Cloeren | 264/171 |
| 4,303,571 | 12/1981 | Jansen et al. | 260/33.6 |
| 4,337,777 | 7/1982 | Pieniak | 128/287 |
| 4,418,123 | 11/1983 | Bunnelle et al. | 428/517 |
| 4,467,595 | 8/1984 | Kramers | 57/225 |
| 4,476,180 | 10/1984 | Wnuk | 428/220 |
| 4,486,507 | 12/1984 | Schumacher | 428/476.1 |

Primary Examiner—Merrell C. Cashion, Jr.
Attorney, Agent, or Firm—Paul Yee

[57] ABSTRACT

A heat-shrinkable elastomer having a first length is produced by uniaxially orienting a copolymer having hard block and elastomeric soft block polymer segments to a second length which is substantially greater than a third length at which partial permanent deformation occurs. Upon removal of the tensioning force, the stretched elastomer naturally relaxes to the third length which is substantially greater than the first length but less than the second length. Upon application of heat, the elastomer shrinks and recovers its elastic properties. The heat-shrinkable elastomer can be coextruded by conventional techniques as a core layer disposed between nonelastic outer layers or skins, and the resulting coextruded elastomer can be uniaxially tensioned as above. Articles or garments such as disposable diapers advantageously use the heat-shrinkable elastomer of the present invention as a means to shirr portions thereof, such as waistbands.

28 Claims, 3 Drawing Sheets

METHOD OF PRODUCING A HEAT SHRINKABLE ELASTOMER AND ARTICLES UTILIZING THE ELASTOMER

CROSS-REFERENCE TO RELATED CASES

This is a continuation of co-pending application Ser. No. 849,916, filed Apr. 8, 1986, now abandoned, which is a continuation-in-part U.S. patent application Ser. No. 606,082 of A. Matray, et al., filed May 1, 1984, now abandoned.

FIELD OF THE INVENTION

The present invention relates to heat-shrinkable elastomers, and in its more specific aspect to heat-shrinkable elastomers especially useful for elastic shirring in garments, such as disposable diapers or like incontinence products.

BACKGROUND OF THE PRESENT INVENTION

Elastic shirring of the garments in selected regions is desirable or essential in order that the garment will conform to the body of the wearer such as at the waist or wrist. This feature is especially true with respect to disposable garments, including plastic garments such as disposable diapers. Hence, the invention, its background and several embodiments, will be described with particular reference to disposable diapers or incontinence garments, but it is understood that the invention is applicable to other garments such as gowns, masks, shoe covers, etc.

Disposable diapers typically have an "hour glass" or general "I-shaped" configuration. The diapers are produced from a continuous web of inner and outer facing sheets and an absorbent batt wherein each waistband area of a diaper module is integrally connected to the waistband area of immediately adjacent diaper modules. (In this regard, see FIG. 2.) The web is cut at the waistband area transverse to the web travel direction to thereby form individual diapers. Thus, the waistband is cut in a cross-machine direction.

Application of elastomeric material to the legbands of disposable diapers has been commercially achieved. However, when elastomeric material is attempted to be applied to waistbands on the same diaper having the legband attached, significant production problems arise. For example, if tension is maintained in the legband direction, the elastomer attached to the waistband tends to bunch the diaper and thus interfere with folding, packaging or other production sequences. We know of no commercial solution to the production problems described above.

Recently, certain proposals have been made regarding heat-set, heat-shrinkable elastomeric materials for use in effecting shirring of disposable garments such as disposable diapers or hospital gowns as evidenced by U.S. Pat. Nos. 3,912,565; 3,819,401; and 3,639,917.

U.S. Pat. No. 3,912,565 to Koch, et al. and U.S. Pat. No. 3,819,401 to Massengale, et al. disclose that flexible polyurethane and plasticized vinyl chloride sheet materials, respectively, are heated, stretched, and cooled to prevent premature shrinkage. In order to prevent premature shrinkage, the elastomeric sheet materials are again heated to permit limited relaxation and cooled to heat set the sheet materials. The heat set sheet materials are then applied to articles and upon application of heat, they shrink to their original lengths thus shirring the articles. As more fully explained with reference to FIG. 1 in Koch, et al. and Massengale, et al., the sheet material is stretched between heated roll 25 and nip rolls 31, 33, then cooled, partially relaxed in heated liquid bath 45 and collected in roll 49. What should be noted in Koch, et al. and Massengale, et al. is that stretching is accomplished by application of external heat, cooled at the stretched condition, then again heated by application of external heat to effect controlled heat shrinkage.

U.S. Pat. No. 3,639,917 to Althouse discloses an elastomer comprising block copolymers that are heat-shrinkable. According to Althouse, the block copolymers are expanded or deformed from an original length at elevated temperatures to achieve a new length and then cooled to maintain the copolymers at the new length of the expanded state. The copolymers of Althouse retain the new length until again heated, at which time shrinkage to the original length occurs. The copolymers of Althouse therefore are expanded from their original length to a new length, maintained at the new length by cooling, and subsequently returned to the original length upon application of heat.

SUMMARY OF THE INVENTION

The elastomer of the present invention which exhibits potential elastic energy recoverable upon heat-shrinking is oriented as by stretching or rolling in one direction without the application of external heat to a length so that when the applied tension is removed, the elastomer relaxes to a permanent deformation length greater than the original length yet less than the stretched length. More significantly, the heat-shrinkable elastomer having an original or first length is stretched in one direction to a substantially greater or second length without the application of external heat as, for example, to at least about 200%. When relaxed, the elastomer assumes a permanent deformation at a third length somewhere between or somewhat intermediate to the first and second lengths. This third length or intermediate state is sometimes known as a preform. The tensioned, preformed elastomer exhibits reduced elastic properties while in the deformed state. Upon the subsequent application of heat, the elastomer shrinks and recovers or assumes its elastic properties. The elastomer, when tensioned at practical or preferred values, exhibits an increase in permanent deformation length with increased tension whereas the conventional elastomers exhibit minimal permanent deformation.

It is significant that heat-setting and cooling of the elastomeric preform is obviated. Tensioning and relaxing the elastomer, which results in uniaxial orientation of the polymer, is performed without the application of external heat, that is at room temperature or ambient conditions (e.g. 70°–75° F. ) although an incidental internal rise in temperature may occur. This procedure is capable of providing the elastomer with heat-shrinkable characteristics. Thus, certain processing steps and associated equipment are eliminated in the commercial application of the elastomer to a garment.

In accordance with one embodiment of the invention, the elastomer is coextruded or laminated with a nonelastic. Preferably, the elastomer and the nonelastic are coextruded as a composite sheet according to known techniques. Desirably, the composite elastomer comprises three layers—an intermediate elastomeric layer and two outer layers. The elastomer may exhibit tackiness and on standing as in roll form may block. The skin layer of inelastic is selected to provide non-blocking or release when the composite material is unrolled, which facilitates processing, such as, guiding, cutting and placement. Further, the elastomer may exhibit poor or no adhesion to many garment materials. Therefore, the oppositely disposed outer layer of the composite which faces the garment is affixed to the garment as with a pressure sensitive or heat-sensitive adhesive. Thus, the composite has these advantages not possessed by the single layer composite.

BRIEF DESCRIPTION OF THE ACCOMPANYING DRAWINGS

Reference will hereinafter be made to the accompanying drawings wherein like reference numerals throughout the various Figures denote like elements and wherein.

DETAILED DESCRIPTION OF THE PREFERRED EXEMPLARY EMBODIMENTS

1. Single Layer Film Embodiment

Figure 1:
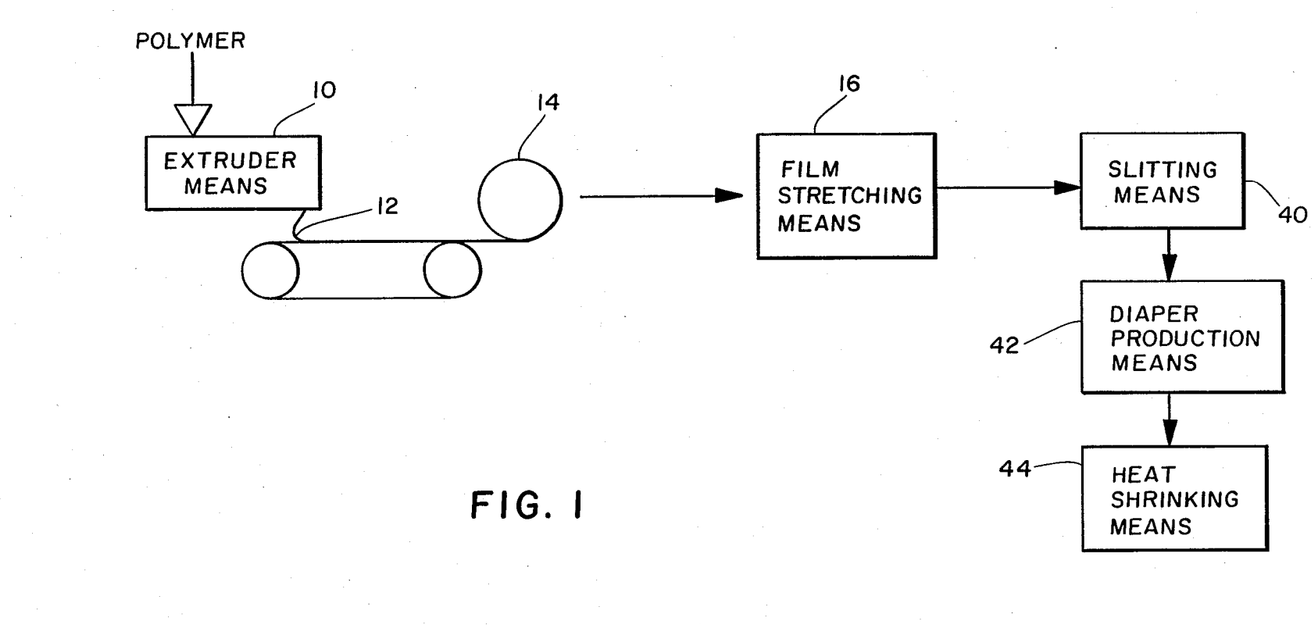
FIG. 1 is a block diagram representing the processing steps of the present invention.

Referring to FIG. 1, it is seen that the process of the present invention begins with the extrusion of the polymer which may be in pellet form by conventional extrusion means 10 to form a film 12 which is preferably subsequently stored in rolls 14 and transported to the next processing station e.g. film stretching 16. Advantageously, the extruded film has a thickness of between about 2 mils to about 4 mils, although other thicknesses are possible in dependence upon the amount of stretching that is needed to achieve the desired degree of article shirring, the specific polymer that is used, the economies of production or the like.

The elastomeric materials employed in the present invention exhibit the elastic properties of natural rubber. In particular, the elastomers, while at room temperature, naturally relax and return to substantially their original length after they have been elongated 50% and then released.

While the term "film" has been used above, the elastomers of the present invention can be produced in other structural forms such as ribbon, thread, tape or the like. For convenience of reference, however, the term "film" will be used hereinafter.

The material employed to produce the elastomer film of the invention consists essentially of a synthetic, thermoplastic rubber. In particular aspects of the invention, the oriented film exhibits a heat shrinkage of at least about 20%, and preferably exhibits a heat shrinkage which ranges from 40–60%. The film material also has a tensile strength at break which is at least about 20 MPa, preferably ranges from 20–40 MPa and more preferably is about 29 MPa. The tensile strength at break is measured according to the procedure of ASTM D638. After it has been activated, the heat shrunk film exhibits a creep value of less than 6%, as measured under a 1.0 MPa stress at 20° C. over a period of 3 weeks. Preferably, the creep value ranges from 0.1–5.75%, and more preferably is about 4.75%. In addition, the oriented unshrunk film exhibits an elastic elongation of at least about 25%, (measured at 500 gm tension) and exhibits a Youngs modulus (measured at 2% elongation) which ranges from 3–15 MPa.

Synthetic rubbers suitable for use with the present invention include, for example, elastomeric films composed of segmented block copolymers represented by the formula $(A-B)_n$. A particularly useful elastomer which is composed of a segmented block copolymer, is a block copolymer having alternating segments of polyamide and polyether block polymers according to the general formula:

wherein $R_1$ represents the polyamide polymer block exemplified by nylon 6, nylon 6,6, nylon 10, nylon 11, and nylon 12 and $R_2$ represents the polyether polymer block exemplified by polyethylene glycol, polypropylene glycol and polytetramethylene glycol and wherein n is an integer. The copolymers in accordance with the above description are commercially available from the ATOCHEM Polymers of Glen Rock, N.J. under the trade name PEBAX. Particularly preferred for the films of the present invention are the PEBAX extrusion grades 2533 and 3533.

Another suitable elastomer composed of a segmented block copolymer is a copolymer made by polymerizing blocks of rigid urethanes with blocks of elastomeric polyethers or polyesters. A representative example of such elastomeric materials is an elastomeric polymer film identified as Deerfield PT-9300 manufactured by Deerfield Co., which is located at South Deerfield, MA. This material is ordinarily not heat shrinkable. However, it can be made heat shrinkable by stretching it at room temperature to an elongation of about 400%. Upon removal of the stretching force, the Deerfield PT-9300 elastic naturally contracts to lose about 57% of the previously applied elongated stretch. A portion of the remaining stretch deformation can be recovered by heating the film to a temperature of about 200° F. Up to about 50% heat shrinkage can be achieved. This heat shrinkable urethane-type film material advantageously does not block or stick to itself. As a result, this material can be extruded, oriented, slit, and wound without the need for a coextruded skin layer. Such skin layers can diminish the heat shrinkage value of the oriented film. In addition, single layer, urethane-type films are less expensive to manufacture.

Other suitable synthetic rubbers are represented by the formula $(A-B)_n-X$. The X represents a coupling agent, and the n is frequently 2, 3 or 4. Representative examples of this type of synthetic rubber include polystyrene/polydiene radial block thermoplastic elastomers and Solprene brand synthetic rubber produced by Phillips Chemical.

Further suitable synthetic rubbers are in the form of particular layered films, which are constructed with a synthetic rubber layer composed of linear block copolymers represented by the formula A-B-A, wherein A is a substantially rigid, inelastic hard block segment and B is an elastomeric soft block segment. Examples of this type of synthetic rubber include layers of EVA and Kraton brank synthetic rubbers. The Kraton rubbers are produced by Shell Oil Company, and are described in U.S. Pat. No. 3,265,765 as linear three-block copolymers of polystyrene/polydiene.

Still other suitable synthetic rubbers are composed of a blend of random polymers. For example, in a particular aspect of the invention, the elastomeric film material composed of a blend of an ethylene/vinyl acetate (EVA) copolymer and an ethylene/propylene/hexadiene terpolymer (EPDM). A representative example of this type of material is Polytrope 377-01, Lot No. 6424 manufactured by A. Schulman Corporation of Akron, Ohio.

The film 12 formed as described previously is then subjected to uniaxial stretching without application of external heat by any conventional film stretching means 16 such as by the differential speed roll process. A particularly preferred differential speed roll suitable for use as film stretching means 16 to stretch films of the present invention is a Marshall and Williams Model D7700 machine direction stretching apparatus. According to well-known principles of differential roll stretching, the film 12 is uniaxially stretched due to the differential speed of low and high-speed rolls. Another method of orientation to induce heat shrinking is by "cold rolling" on multi-stack rolling mills under external pressure similar to that used in rolling thin metal sheet such as aluminum foil. Regardless of the orientation method, however, the common phenomenon accomplished is an increase of the dimension in the direction of orientation by a corresponding decrease in thickness.

Conventional, uniaxially stretched polymeric films are typically preheated to a temperature at or above the second order phase transition temperature. The conventional film is then stretched while at such elevated temperatures and subsequently cooled while being maintained in its stretched condition. Such preheating is important to conventional films so as to ensure proper stretching and orientation thereof.

Preheating is completely unnecessary with the present invention, however. Some heat may be generated during the uniaxial stretching of the film 12 due to frictional forces or the like particularly if differential speed rolls are utilized to effect film stretching, but it has been surprisingly found that such temperature is sigiificantly below (e.g. substantially less than 175° F.) the temperature at which deformation relaxation of the copolymer film begins to occur. That is, even though some heat may be frictionally generated during film stretching, the temperature at which the film of the present invention reaches is substantially below the temperature at which relaxation of the deformation occurs. Heat setting, of course, contemplates that the temperature must be at or above the temperature at which deformation relaxation begins to occur. (See, U.S. Pat. No. 3,912,565 at column 3, lines 28-38.) Thus, no heat-setting of the oriented film of the present invention is required in direct contrast to what was conventionally thought to be essential in this art.

The amount of uniaxial stretching of the elastomer films of this invention is important to achieve adequate shrinkage and thus shirring of an article utilizing the film. In accordance with the present invention, uniaxial tensioning is accomplished so that the film is stretched to an elongated length significantly greater than that length at which permanent deformation occurs. Upon removal of the applied tension, the film will naturally relax (e.g. without being induced to relax by the application of heat) to a length greater than the original length, corresponding to the amount of permanent deformation which has been imparted thereto. Thus, the differential length between the permanent deformation length and the original, pre-stretched length is available for heat shrinkage. Upon application of heat therefore (e.g. at or above 175° F.) the stretched film will further be induced to relax and shrink. That is, a large portion of the differential length of the stretched film between the original length and the permanent deformation length is present as permanent deformation which is capable of recovery upon application of heat.

The film of the present invention is uniaxially stretched to achieve between about 200% to about 700% elongation per unit length of the film. It has been discovered that when the film of the present invention is uniaxially stretched within the ranges noted above, it will exhibit some natural relaxation upon removal of the stretching force but such relaxation will not proceed below the respective permanent deformation length. The length of the film corresponding to the amount of permanent deformation imparted thereto is therefore dependent upon the amount of uniaxial tensioning to which the film is subjected. However, for uniaxial stretching in the range of about 200% to 700%, the permanent deformation length will be between about 20% and 60% of the film's elongated length. That is, the amount of permanent deformation available for heat shrinkage will be about 20% to about 60% of the stretched length of the film when stretched between about 200% to about 700% (e.g. when stretched 3× to 8× of the original length).

It has been discovered that the rate at which the uniaxial stretching is applied to the elastomer can significantly affect the heat shrinkage value of the oriented elastomer. To improve the effectiveness and efficiency of the orienting process, the elastomer is stretched at a rate of at least about 9 in/min/in, preferably is stretched at a rate of at least about 20 in/min/in, and more preferably, is stretched at a rate of at least about 40 in/min/in.

The amount of permanent deformation which is imparted to the film of the present invention will, therefore, determine the degree of heat shrinkage which is available to adequately shirr that portion of an article with which it is associated. The particularly useful oriented films of the present invention exhibit a percent heat shrinkage value of at least about 20%, and preferably exhibit a percent heat shrinkage of at least about 40%. It has been found that a permanent deformation of between about 40–60% of the elongated length (termed the "unrestricted shrinkage") will advantageously translate into between about 30–45% shrinkage (termed the "restricted shrinkage") when the uniaxially stretched film is attached to a portion of a flexible garment such as the waistband of a disposable diaper. That is, since the flexible article will interfere or restrict the shrinkage of the film somewhat, complete return to the original, prestretched film length does not occur upon heat shrinkage. Nevertheless, when the film of the present invention is uniaxially stretched as described above (e.g. between about 20–60% permanent deformation or elongation based upon the final elongation to which the film is subjected), desirable article shirring can occur.

Subsequent to stretching, the film of the present invention is advantageously slit by conventional film slitting means 40 along the direction of permanent deformation (that is, parallel to the uniaxial stretching direction) to form ribbons which are advantageously ⅜" to ½" wide but other widths are, of course, possible depending upon the intended application. The ribbons can then be level wound according to known techniques into spools for use in diaper production equipment 42.

Figure 2:
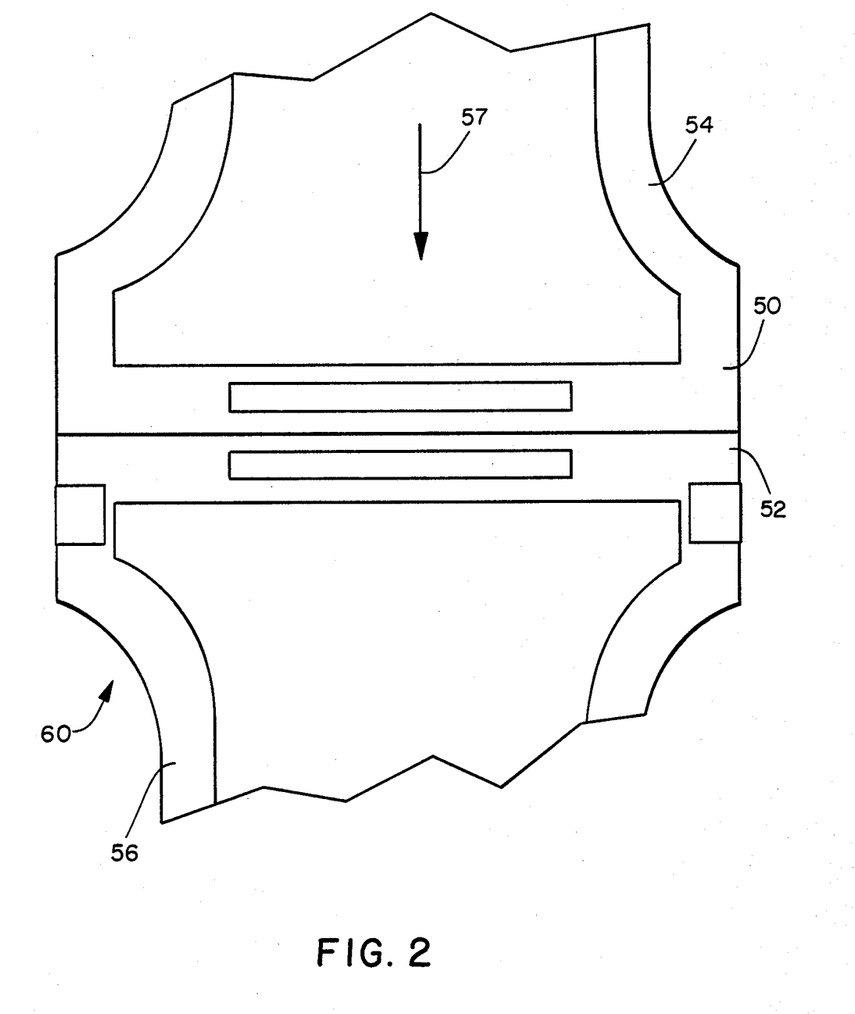
FIG. 2 is a schematic plan view of a portion of a continuous diaper web during manufacture having ribbons of the film of the present invention attached to the waistband area thereof and shown prior to being heat-shrunk.

The ribbons are preferably cut to desired lengths (advantageously about 6") while still in their heat-shrinkable elongated condition and adhesively secured to waistband portions 50, 52 of diapers 54, 56 as the connected web 60 travels in the machine direction (arrow 57 in FIG. 2). Adhesives suitable for bonding ribbons of the films of this invention to the waistband areas of the diapers are commercially available from the Findley Co. under the designation 191-335B and the National Starch Co. under the designation 34-5506. It is presently contemplated that a stack of folded diapers having ribbons of the heat-shrinkable elastomeric film of the present invention will be collectively subjected to heat by suitable heat shrinking means 44 so as to cause heat shrinkage of the ribbons to thus shirr the waistband portions of the diapers.

2. Multilayer Film Embodiment

A further embodiment of the present invention resides in the coextrusion of the elastomeric copolymers described hereinabove with nonelastic polymers such as ethylene vinyl acetate (EVA), EVA ionomers such as, Plexar 3, Plexar 102, and Surlyn 1702 and 1705, (Plexar 3 and Plexar 102 are commercially available from the Chemplex Corporation while Surlyn 1702 and 1705 are commercially available from DuPont) and polyethylene or the like to advantageously produce a composite elastomer film which is heat-shrinkable and also exhibits a pleasing hand. Skin compatability of elastic waistbands is desirable when the films of the present invention are used as waistbands for disposable diapers. According to a particular embodiment of the present invention, a polyether/polyamide copolymer is coextruded as the core or intermediate layer with surface exposed layers or outer layers of nonelastic polymers. Although the outer layers may not be heat-shrinkable, they will not significantly affect the heat shrinkage of the core of such an extent that adequate shirring of the garment will not occur owing to the superior heat-shrinking capabilities of the core layer film.

The coextrusion of layers of diverse polymers or thermoplastic materials is, in and of itself, well known in the art as generally exemplified by U.S. Pat. Nos. 3,557,265 to Chisholm, et al. and 3,479,425 to Lefevre, et al. Coextrusion of diverse polymer materials is typically accomplished utilizing a multi-manifold coextrusion die or a single manifold die with combining adaptors which permit the melt lamination of multiple layers of dissimilar polymer materials. One particularly preferred combining adaptor which can be advantageously employed to achieve coextruded films of this invention is described in U.S. Pat. No. 4,152,387 to Cloeren.

Figure 3:
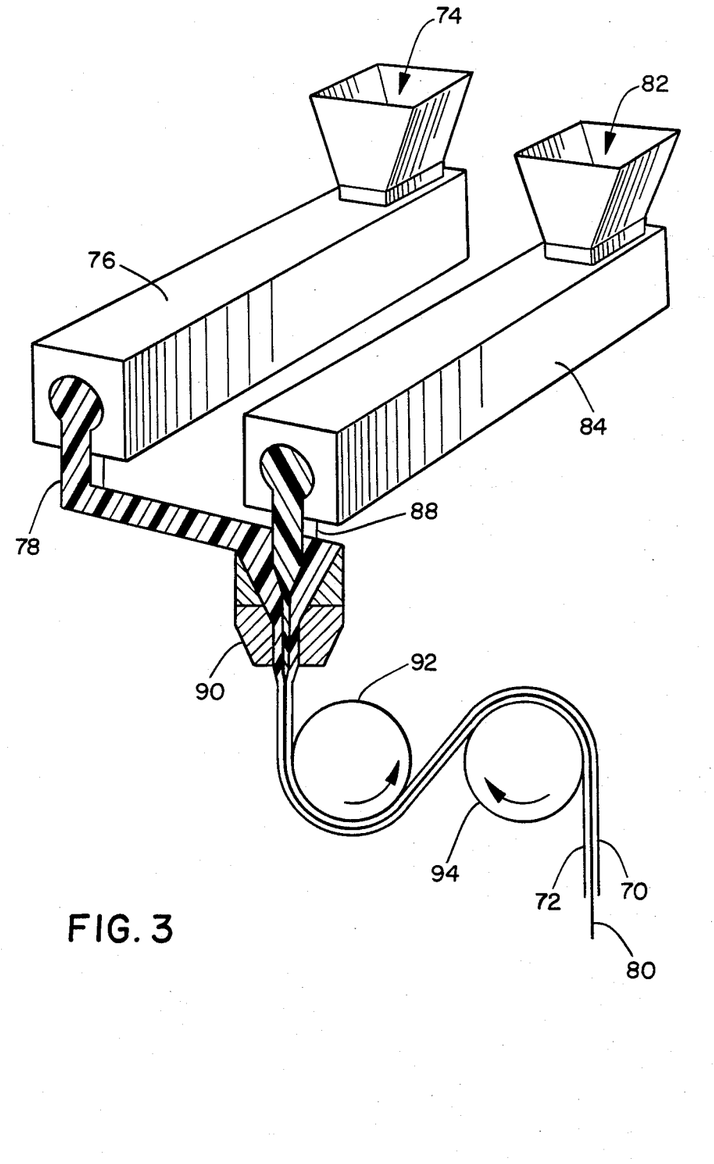
FIG. 3 is a schematic view of a means to coextrude the multilayer film embodiment of this invention.

A conventional means of producing coextruded multilayer films of this invention is schematically depicted in accompanying FIG. 3. As shown therein the outer nonelastic layers 70, 72 are formed by melt extruding the nonelastic polymers 74 by means of extruder 76. Similarly, the elastic core layer 80 is formed by melt extrusion of the elastic polymer 82 (e.g. preferably PEBAX extrusion grades 2533 or 3533) by means of extruder 84. The melt extruded polymers 74, 82 are then passed to combining adaptor 90 via conduits 78, 88, respectively. As schematically shown, the elastic polymer 82 melt laminates with the nonelastic polymer 74 to form a core layer 80 of the elastic polymer 82 which is sandwiched between outer layers 70, 72 of the nonelastic polymer 74.

Although the temperature of the combining adaptor 90 is dependent upon the polymers utilized, it is preferable to maintain the temperature thereof between about 360° F. to about 500° F. (preferably about 400° F.) to advantageously form the coextruded films of this invention. Additionally, it is preferable that the total thickness of the coextruded film be between about 2 to about 5 mils with between about 2 to about 4 mils being particularly preferred, although other film thicknesses could be utilized in dependence upon the final stretched thickness that is desired. The coextruded film contacts chill rolls 92, 94 so as to cool it to substantially maintain the extruded thickness thereof. Another means for forming the multilayers is by blown coextrusion using a circular die with coaxial flow channels corresponding to the individual layers of the composite. The coextruded film can then be oriented by conventional stretching means 16, slit into ribbons by slitting means 40, applied to diapers in diaper production means 42 and heat shrunk by heat shrinking means 44 as described above with reference to FIG. 1.

The core layer of elastic polyether/polyamide block polymer is preferably the major constituent (based on percent of coextruded film by volume) present in the resulting coextruded film. The core layer therefore preferably is present in the coextruded film in an amount between about 70% to about 90% by volume, with the balance being substantially evenly distributed between each of the outer layers.

The behavior of the coextruded composite or laminate of this invention is similar to the behavior of the single layer films described above. That is, when the composite is uniaxially oriented to a length between about 200% to about 700% of the original length, permanent deformation will be imparted thereto at a length generally between about 20% to about 60% of the elongated length. Upon removal of the tension force, the coextruded film will likewise naturally (e.g. without application of heat) relax to the length indicative of the permanent deformation imparted thereto (e.g. the permanent deformation length). Thus, the differential in length between the elongated length and the permanent deformation length is available as a shrinkage length so that when heat is applied thereto (generally at temperatures near 200° F.) the film substantially relaxes and shrinks to recover its elastic properties. To more effectively process the elastomer, the coextruded composite is oriented and stretched at a rate of at least about 9 in/min/in, preferably is stretched at a of at least about 20 in/min/in, and more preferably, is stretched at a rate of at least about 40 in/min/in.

As briefly noted above, the outer layers or skins of the composite tend to interfere somewhat with heat shrinkage of the overall film due to the nonelastic nature of the skins. However, such interference is not of a degree which masks the heat shrinkability of the composite. Since the outer layers are nonelastic, uniaxial tensioning of the coextruded film also permanently deforms such outer layers. However, the overall coextruded film will still naturally relax to between about 20%–60% of the elongated length upon removal of the tensioning force owing to the presence of the elastic core layer.

The intralaminar bonding strength between the outer layers and core layer is preferably at least 1200 grams/in to ensure that the layers remain laminated to one another when subjected to uniaxial orientation of up to about 700% elongation.

The use of microwave energy as the means to heat shrink both the single layer and multilayer film embodiments of the invention is also possible. It has been discovered that when the elastomers of the invention are exposed to microwave energy of 2450 MHz and between 3-6 kilowatts for about 5-10 seconds, adequate heat shrinkage occurs. That is, when exposed to microwave energy the elastomers shrink between about 20% to about 60% of the stretched length. For example, a particular heat-shrinkable elastomeric ribbon of this invention formed of a core layer of PEBAX extrusion grade 3533 coextruded with outer layers of Plexar 102 and uniaxially stretched to 4× the original length (e.g. 300% stretch) to achieve a ribbon thickness of 1.5 mils, exhibited at least 20% heat shrinkage when affixed to the inside waistband area of a diaper when the ribbon-affixed diaper was exposed to microwave energy of 2450 MHz and between 3-6 kilowatts for about 5-10

The following examples are provided to give a more detailed understanding of the invention. The particular proportions, materials and parameters are exemplary and are not intended to specifically limit the scope of the invention.

EXAMPLE 1

Single layer films were prepared from various commercially available polymers by the chill roll cast method using a 36" extrusion die at die temperatures of 400°–425° F. and at line speeds of 120 fpm for 2 mil and 60 fpm for 4 mil film. Heat shrinkability of film samples was examined by preparing 1"×10" strips of film cut in the machine direction. The film samples were then marked at initial lengths of 4" (101.6 mm) and were conditioned at 72° C., 55% relative humidity for 24 hours. Subsequent to conditioning, individual samples were stretched on an Instron Tensile Tester, at 72° F. and 55% relative humidity, to 100%, 300% and 500% elongation (i.e. 2×, 4× and 6× stretch). The initial jaw span of the Instron Tensile Tester was 4.5 inches which translated into film sample lengths of 9 inches at 100% elongation; 18 inches at 300% elongation and 27 inches at 500% elongation, respectively. In each instance, the rate of stretching was 1000 mm/min. The stretched samples were again conditioned at 72° F. and 55% relative humidity for 24 hours.

Permanent deformation was then measured as a percentage of the original 4 inch film length according to the formula:

$$\% \text{ Permanent Deformation} = \frac{L_f - L_o}{L_o} \times 100$$

wherein $L_o$ represents the original film length and $L_f$ represents the final length to which the film relaxes without application of heat after the applied tension is removed.

To determine the amount of heat shrinkability which is imparted to the films, the stretched film samples were then heat shrunk by subjecting the samples to 175° F. for 5 seconds. The length of each film sample subsequent to heat shrinkage ($L_{fl}$) was measured and the percent heat shrinkability was calculated by the formula:

$$\% \text{ Heat Shrinkability} = \frac{L_f - L_{fl}}{L_f} \times 100$$

wherein $L_f$ is the length of the film as defined above with respect to percent permanent deformation.

In order to determine the elastic nature of the heat shrink materials, the hysteresis ratio of each sample was calculated using an Instron Tensile Tester equipped with an integrator unit. In each instance, the stretched and heat shrunk samples were secured between the jaws of the Instron Tensile Tester to establish a 4" initial length regardless of the sample size subsequent to heat shrinkage. Each sample was then stretched to 100% elongation at 500 mm/min stretching rate. Thus all samples were elongated to 8 inches. During the elongation, the integrator unit measured the area under the stretch curve and the resulting data was noted. When 100% elongation occurred, the integrator unit was reset and relaxation of the Instron jaws was initiated until the initial 4 inch separation length was achieved. During relaxation, the integrator unit measured the area under the relaxation curve. The hysteresis ratio (HR) was therefore calculated as follows:

$$HR = \frac{\text{Area under stretching curve}}{\text{Area under relaxation curve}}$$

Since a true elastomer (e.g. natural rubber) will exhibit a hysteresis ratio of about 1.0, measurement of the hysteresis ratios of the tested films provided an indication of their elasticity subsequent to heat shrinkage. Thus single layer films which exhibited heat shrinkage of between about 40% to about 60% or more while yet having a hysteresis ratio of less than 2.0 were suitable for use as elastic waistbands for disposable diapers. The results are tabulated below in Table I.

TABLE I

| Sample No. | Film | Extruded Film Thickness | % Elongation | % Permanent Deformation | % Heat Shrinkage | Hysterisis Ratio (HR) |
|---|---|---|---|---|---|---|
| 1 | PEBAX-2533 | 4 mils | 0 | — | 1.6 | 1.4 |
|   |   |   | 100 | 1.4 | 2.6 | 1.3 |
|   |   |   | 300 | 74.2 | 37.2 | 1.3 |
|   |   |   | 500 | 261.0 | 63.9 | 1.3 |
| 2 | PEBAX-2533 | 2 mils | 0 | — | 3.9 | 1.4 |
|   |   |   | 100 | 1.6 | 4.9 | 1.4 |
|   |   |   | 300 | 86.5 | 42.8 | 1.3 |
|   |   |   | 500 | 268.0 | 65.4 | 1.3 |
| 3 | KRATON 2703G[1] | 6 mils | 0 | — | 5.1 | 3.2 |
|   |   |   | 100 | 6.3 | 5.2 | 3.2 |
|   |   |   | 300 | 42.4 | 3.3 | 3.5 |
|   |   |   | 500 | 73.6 | 5.9 | 2.4 |
| 4 | KRATON 2109 | 5.9 mils | 0 | — | 5.5 | 1.7 |

TABLE I-continued

| Sample No. | Film | Extruded Film Thickness | % Elongation | % Permanent Deformation | % Heat Shrinkage | Hysterisis Ratio (HR) |
|---|---|---|---|---|---|---|
| | | | 100 | 3.5 | 7.0 | 1.7 |
| | | | 300 | 18.1 | 8.4 | 1.6 |
| | | | 500 | 27.1 | 7.9 | 1.5 |
| 5 | KRATON 2103 | 3 mils | 0 | — | 9.7 | 1.6 |
| | | | 100 | 1.1 | 11.6 | 1.6 |
| | | | 300 | 2.9 | 13.1 | 1.6 |
| | | | 500 | 4.1 | 12.9 | 1.7 |
| 6 | TUFTANE-410[2] | 2 mils | 0 | — | 0.5 | 1.8 |
| | | | 100 | 1.4 | 6.4 | 1.50 |
| | | | 300 | 13.4 | 11.3 | 1.42 |
| | | | 500 | 51.6 | 22.1 | 1.44 |
| 7 | NATURAL RUBBER (CONTROL) | 12 mils | 0 | 0 | 0 | 1.01 |
| | | | 100 | 1.4 | 1.0 | 1.05 |
| | | | 300 | 2.4 | 1.0 | 1.07 |
| | | | 400 | 5.3 | 2.0 | 1.05 |
| | | | 500 | 6.3 | 2.0 | 1.08 |

[1]Kraton is a trade name of the Shell Oil Co.
[2]Tuftane is a trade name of Goodrich Chemical.

EXAMPLE II

Coextruded multilayer films having an elastomeric film core layer and nonelastomeric film outer layers were prepared using a conventional combining adaptor commercially obtained from the Cloeren Co. and was the type described in U.S. Pat. No. 4,152,387. Testing for percent permanent deformation, percent heat shrinkage and hysteresis ratio were conducted as in Example I, above, and the results are tabulated in Table II below.

EXAMPLE III

Example II was repeated with the exceptions that Plexar 102 (commercially available from the Chemplex Corp.) and Surlyn-1702 (commercially obtained from DuPont) were utilized as outer layers in 10%/80%/10% relative volume compositions (e.g. outer layer/core layer/outer layer) with a core layer of PEBAX 2533 and 3533. Testing for percent heat shrinkage and hysteresis ratio were conducted as in Example I and the results thereof are tabulated in Table III below.

TABLE II

| Sample No. | Film (outer layer/core layer/outer layer) | Extruded Film Thickness | % Stretch | % Permanent Deformation | % Heat Shrinkage | Hysteris Ratio (HR) |
|---|---|---|---|---|---|---|
| 8 | PE/Solprene/PE[1] (33% core layer) | 5 mil | 0 | — | 0.6 | 3.6 |
| | | | 100 | 10.2 | 6.3 | 3.4 |
| | | | 300 | 90.9 | 25.1 | 3.1 |
| | | | 500 | 74.2 | 20.0 | 1.7 |
| 9 | PE/Kraton 2109/PE[2] (33% core layer) | 5 mil | 0 | — | 1.6 | 3.9 |
| | | | 100 | 11.2 | 7.6 | 3.9 |
| | | | 300 | 111.4 | 25.1 | 3.4 |
| | | | 500 | 103.7 | 17.8 | 2.1 |
| 10 | PE/EVA/Kraton 2109[3] (33% core layer) | 5 mils | 0 | — | 0.6 | 3.1 |
| | | | 100 | 5.5 | 6.7 | 2.8 |
| | | | 300 | 58.7 | 34.7 | 2.1 |
| | | | 500 | 71.9 | 29.9 | 2.0 |
| 11 | Plexar 3/PEBAX 2533/ Plexar 3[4] (90% core layer) | 4 mils | 0 | — | 0.8 | 1.75 |
| | | | 100 | 4.8 | 3.5 | 1.74 |
| | | | 300 | 115.2 | 43.7 | 1.53 |
| | | | 500 | 277.0 | 60.4 | 1.61 |
| 12 | Plexar 3/PEBAX 2533/ Plexar 3 (35% core layer) | 6.9 mils | 0 | — | 0.8 | 3.81 |
| | | | 100 | 12.1 | 8.2 | 3.36 |
| | | | 300 | 177.2 | 43.1 | 3.63 |
| | | | 500 | 376.0 | 51.3 | 4.00 |
| 13 | EVA/PEBAX 2533/EVA[5] (74% core layer) | 3.6 mils | 0 | — | 0.6 | 2.04 |
| | | | 100 | 4.8 | 3.6 | 2.05 |
| | | | 300 | 129.1 | 46.5 | 2.35 |
| | | | 500 | 289.0 | 61.4 | 2.18 |
| 14 | Plexar 3/PEBAX 3533/ Plexar 3 (67% core layer) | 4.9 mils | 0 | — | 2.6 | 2.18 |
| | | | 100 | 7.5 | 5.9 | 2.07 |
| | | | 300 | 160.9 | 44.7 | 2.17 |
| | | | 500 | 309.0 | 56.1 | 2.30 |
| 15 | Plexar 3/PEBAX 4033/ Plexar 3 (66% core layer) | 3.4 mils | 0 | — | 0.4 | 3.19 |
| | | | 100 | 14.3 | 5.6 | 3.11 |
| | | | 300 | 181.8 | 34.9 | 3.81 |
| | | | 500 | 349.0 | 42.9 | 4.19 |

[1]PE = Chemplex 3404-D obtained from Chemplex Corp.; Solprene = solprene 418 obtained from Phillips Chemical
[2]PE = Chemplex Plexar copolymer.
[3]PE = Chemplex 3404-D; EVA = Chemplex 3312
[4]Plexar 3 is trade name of Chemplex Corp.
[5]EVA = Chemplex 4634

TABLE III

| Sample No. | Film (outer layer/core layer/outer layer) | Extruded Film Thickness | % Stretch | % Permanent Deformation | % Heat Shrinkage | Hysteris Ratio (HR) |
|---|---|---|---|---|---|---|
| 16 | Plexar 102/Pebax-2533/ Plexar 102* (10/80/10) | 3 mils | 100 | 7 | 5 | 2.20 |
|  |  |  | 200 | 60 | 28 | 2.32 |
|  |  |  | 300 | 142 | 36 | 1.93 |
|  |  |  | 400 | 225 | 43 | 2.09 |
|  |  |  | 500 | 277 | 51 | 1.71 |
| 17 | Surlyn 1702/Pebax-2533/ Surlyn 1702** (10/80/10) | 3 mils | 100 | 5 | 6 | 2.43 |
|  |  |  | 200 | 37 | 22 | 2.06 |
|  |  |  | 300 | 102 | 43 | 2.26 |
|  |  |  | 400 | 179 | 52 | 2.25 |
|  |  |  | 500 | 265 | 62 | 2.15 |
| 18 | Plexar 102/Pebax-3533/ Plexar 102 (10/80/10) | 3 mils | 100 | 6 | 4 | 1.73 |
|  |  |  | 200 | 42 | 19 | 1.80 |
|  |  |  | 300 | 120 | 34 | 1.68 |
|  |  |  | 400 | 208 | 47 | 1.76 |
|  |  |  | 500 | 269 | 52 | 1.56 |
| 19 | Plexar 102/Pebax-3533/ Plexar 102 (10/80/10) | 2 mils | 100 | 7 | 5 | 2.30 |
|  |  |  | 200 | 53 | 23 | 1.91 |
|  |  |  | 300 | 104 | 33 | 2.04 |
|  |  |  | 400 | 224 | 39 | 1.6 |
|  |  |  | 500 | 266 | 51 | 1.9 |

*Plexar 102 is an ionomer resin commercially available from Chemplex Corp.
**Surly 1702 is an ionomer resin commercially available from duPont de Nemours Co.

EXAMPLE IV

Samples of elastomeric film composed of Deerfield PT-9300 and Polytrope 377-01 material were processed in accordance with the method of the invention and exhibited the characteristics set forth in Table IV below.

The above-identified Deerfield and Polytrope materials were processed employing an inline stretching device which included two cooperating pairs of nip rollers. Each pair of nip rollers contacted the elastomer material with a generally nonslip engagement in the nip formed therebetween. The first pair of nip rollers, however, was driven to provide a peripheral surface speed that was less than the peripheral surface speed provided by the second nip roller pair. As a result, the length of elastomer material located between the two sets of nip rollers became drawn out and stretched by the tension exerted by the second nip roller pair. The distance between the two sets of nip rollers and the relative difference between the two peripheral surface speeds provided by the two sets of nip rollers were selectively adjusted to impart the desired amount of elongation and the desired rate of elongation to the elastomer material. In particular, the elastomer material was stretched at rates of up to 45.45 in/min/in. This stretching rate is to be contrasted with the stretching rate of about 4.37 in/min/in imparted by Instron machine stretching technique described in the previous examples.

TABLE IV

| Film | Sample No. | % Elongation (Stretch Orientation) | Shrunk Length (mm) | Gauge (mil) | Elastic Tension (gm) | % Elongation (at 500 gm load) |
|---|---|---|---|---|---|---|
| Deerfield PT-9300 3 mil thickness extruded | 20 | 500 | 63 | 2.33 | 242 | 62 |
|  | 21 | 500 | 62 | 1.98 | 253 | 55 |
|  | 22 | 600 | 58 | 1.70 | — | 67 |
|  | 23 | 600 | 57 | 1.65 | 258 | 55 |
|  | 24 | 600 | 58 | — | — | 42 |
| Polytrope 377-01 3 mil thickness extruded |  |  |  |  |  |  |
| Samples 24 & 25 3-layer film | 24 | 200 | 64 | 1.62 | 209 | 17 |
|  | 25 | 300 | 51 | 1.45 | 246 | 12 |
|  | 26 | 300 | 38 | 1.23 | 202 | 40 |
| Samples 26–28 1-layer film | 27 | 200 | 48 | 1.56 | 174 | 75 |
|  | 28 | 100 | 65 | 1.93 | 124 | 223 |

The shrinkage value in Table IV was determined as follows:

A 7/16 in wide oriented ribbon sample was prepared and marked to define a length of 100 mm. The ribbon was placed in a water bath set at a temperature of 140° F. for a period of five seconds to heat activate and shrink the ribbon. After this period the ribbon was removed from the water bath, and the length of the ribbon between the marks was remeasured and recorded.

The percent elongation value in Table IV was determined as follows:

A 7/16 in wide oriented ribbon was prepared and marked to define a length of 100 mm. One end of the ribbon was placed in a clip on a vertical test stand, and a 500 gm weight was placed on the other end of the ribbon to elongate it. After the weight had been applied for a period of 30 sec, the length of the ribbon between the marks was measured and the percent elongation was calculated. The procedure was performed at a temperature of 73.4° C. and a relative humidity of 50%.

The gauge value in Table IV was determined as follows:

A template having an area of 95.22 square inches was employed to cut a film sample, and the sample was weighed to the nearest milligram. The gauge was then calculated employing the following formula:

$$\text{Gauge} = \frac{61.024 \times \text{Sample weight (grams)}}{\text{Density (grams per cc)} \times \text{Area (sq. in.)}}$$

The tension value in Table IV was determined as follows:

A 7/16 in wide oriented ribbon was prepared and marked to define a length of 100 mm. The ribbon was then heat activated in a water bath employing the procedure previously described. The ribbon was placed in the jaws of an Instron tensile tester and elongated to stretch the marked 100 mm portion to a length of 190 mm (90% elongation). After the stretching had been held for a period of one minute, the tension force measured by the Instron machine was recorded. For this procedure the temperature was 73.4° F., and the relative humidity was 50%.

From the above examples, it is readily apparent that both the single layer and coextruded elastomeric polymer films can exhibit satisfactory percent heat shrinkability (e.g. between about 30–60%) when they are stretched and oriented with elongation values of between about 200% to about 500%. When the films are applied to the waistbands of disposable diapers, for example, adequate shirring is achieved. For conventional films, the percent heat shrinkability decreased as the percent film stretch increased from 300% to 500%, while in direct contrast, the films of this invention increased in percent heat shrinkage as the film stretch increased from 300% to 500% (e.g. compare sample nos. 4–5 to 1–2; 8–10 to 11–19). Sample Nos. 3 and 6, although increasing somewhat in percent heat shrinkability did not exhibit the requisite heat shrinkability useful for elastically shirred articles. Thus, the films of the present invention now make it economically feasible to produce disposable diapers having elastic waistbands which exhibit the necessary amount of heat shrinkability to achieve sufficient shirring. Moreover, the films of the present invention overcome many of the commercial and production disadvantages of conventional heat-shrinkable elastomers since no heat setting is required in order to achieve the above-described advantages.

It will be readily apparent to a person having ordinary skill in the art that various changes and modifications may be made without departing from the spirit of the invention. All of such changes and modifications are contemplated as being within the scope of the invention as defined by the subjoined claims.

What is claimed is:

1. A method for producing a heat-shrinkable elastomer, comprising the steps of:
   (a) uniaxially orienting an elastomer which has a first length and consists essentially of a synthetic rubber, said orienting conducted without the application of external heat at an elongation rate of at least about 9 in/min/in to uniaxially orient said elastomer above about 200% elongation to as second length which is substantially greater than a third length at which permanent deformation of said elastomer occurs; and
   (b) releasing the uniaxial orientation applied according to step (a) to allow said elastomer to naturally relax to said third length, said third length being substantially greater than said first length, said relaxed elastomer thereby having a heat shrinkage value of at least about 40 percent, and said heat-shrinkable elastomer produced without heat setting.

2. A method as recited in claim 1, wherein said third length is within the range of aobut 40–60% of said second length.

3. A method as recited in claim 1, wherein said elastomer is uniaxially oriented at an elongation rate of at least about 40 in/min/in.

4. A method as recited in claim 1, wherein asid elastomer consists essentially of a copolymer of alternating polyamide and polyether repeat block polymer segments.

5. A method as in claim 4, wherein said elastomer is uniaxially oriented between about 200% to about 700% elongation to achieve said second length.

6. A method as recited in claim 4, wherein said copolymer has the formula:

wherein $R_1$ is a polyamide selected from the group consisting of nylon 6, nylon 10, nylon 11, nylon 12 and nylon 6,6; $R_2$ is a polyether selected from the group consisting of polyethylene glycol, polypropylene glycol and polytetramethylene glycol; and n is an integer.

7. A method as recited in claim 1, wherein said elastomer consists essentially of a copolymer of substantially rigid urethane block segments and elastomeric soft block segments, said soft block segments selected from the group consisting of polyethers and polyesters.

8. A method as recited in claim 1, wherein said elastomer consists essentially of a material composed of a mixture of an ethylene/vinyl acetate copolymer and an ethylene/propylene/hexadiene terpolymer.

9. A method as recited in claim 7, wherein said elastomer is uniaxially oriented between about 200% to about 700% elongation to achieve said second length.

10. A method as recited in claim 8, wherein said elastomer is uniaxially oriented between about 200% to about 700% elongation to achieve said second length.

11. A method of manufacturing an article having a portion which is elastically shirred, said method comprising the steps of:
   (a) forming a heat-shrinkable elastomer by uniaxially orienting an elastomer having a first length and consisting essentially of a synthetic rubber, said orienting being conducted without the applicaiton of external heat at an elongation rate of at least about 9 in/min/in to uniaxially orient said elastomer above about 200% elongation to a second length substantially greater than a third length at which permanent deformation of said elastomer occurs, and releasing the uniaxial orientation to allow the elastomer to naturally relax to said third length which is substantially greater than said first length, thereby providing said elastomer with a heat shrinkage value of at least about 40% and producing said heat-shrinkable elastomer without heat setting;

(b) affixing the elastomer formed according to step (a) to said portion of the article in a direction generally parallel to the desired direction of shirr; and (c) heat shrinking said affixed elastomer to thereby elastically shirr said portion of the article whereby said elastomer upon heat shrinkage becomes substantially elastomeric.

12. A method of producing a heat-shrinkable elastomer, comprising the steps of:

(a) uniaxially orienting a composite elastomer having a first length, and including outer layers of a nonelastomer and a core layer, the core layer disposed between the outer layers and composed of an elastomer selected from the group consisting of (i) a material consisting essentially of alternating polyamide and polyether repeat block polymer segments, and (ii) a material consisting essentially of a mixture of an ethylene/vinyl acetate copolymer and an ethylene/propylene/hexadiene terpolymer, said orienting being conducted without the application of external heat at an elongation rate of at least about 9 in/min/in to uniaxially orient said elastomer above about 200% elongation to a second length substantially greater than a third length at which permanent deformation of said elastomer occurs; and (b) releasing the uniaxial orientation applied according to step (a) to allow said elastomer to naturally relax to said third length which is substantially greater than said first length, said relaxed elastomer thereby having a percent heat shrinkage of at least about 40%, and said heat-shrinkable elastomer produced without heat setting.

13. A method as in claim 12, wherein prior to step (a) said composite elastomer is formed by melt laminating a coextrusiuon of said core and outer layers.

14. A method as in claim 12, wherein said core layer is between about 70% to about 90% by volume of said elastomer.

15. A method as in claim 12, wherein said core layer is a copolymer having the formula:

wherein $R_1$ is a polyamide selected from the group consisting of nylon 6, nylon 10, nylon 11, nylon 12 and nylon 6,6; $R_2$ is a polyether selected from the group consisting of polyethylene glycol, poypropylene glycol and polytetramethylene gylcol; and n is an integer.

16. A method as in claim 10, wherein said third length is between about 20% to about 60% of said second length.

17. A method as in claim 12, wherein step (a) is conducted so as to uniaxially orient said elastomer to a first length which is between about 200% to about 700% of said first length.

18. A method as recited in claim 1, wherein said elastomer is uniaxially oriented at an elongation rate of at least about 20 in/min/in.

19. A method as recited in claim 4, wherein said elastomer is uniaxially oriented at an elongation rate of at least about 20 in/min/in.

20. A method as recited in claim 7, wherein said elastomer is uniaxially oriented at an elongation rate of at least about 20 in/min/in.

21. A method as recited in claim 8, wherein said elastomer is uniaxially oriented at an elongation rate of at least about 20 in/min/in.

22. A method as recited in claim 11, wherein said elastomer is unaiaxially oriented at an elongation rate of at least about 20 in/min/in.

23. A method as recited in claim 12, wherein said elastomer is uniaxially oriented at an elongation rate of at least about 20 in/min/in.

24. A method as recited in claim 4, wherein said elastomer is uniaxially oriented at an elongation rate of at least about 40 in/min/in.

25. A method as reicted in claim 7, wherein said elastomer is uniaxially oriented at an elongation rate of at least about 40 in/min/in.

26. A method as recited in claim 8, wherein said elastomer is uniaxially oriented at an elongation rate of at least about 40 in/min/in.

27. A method as recited in claim 11, wherein said elastomer is uniaxially oriented at an elongation rate of at least about 40 in/min/in.

28. A method as recited in claim 12, wherein said elastomer is uniaxially oriented at an elongation rate of at least about 40 in/min/in.

* * * * *